United States Patent [19]
Kay et al.

[11] Patent Number: 5,766,547
[45] Date of Patent: Jun. 16, 1998

[54] VACUUM PUMP DEODORIZING APPARATUS AND METHOD

[75] Inventors: Thomas T. Kay, Mancos; Hal A. Reigi, Cortez, both of Colo.

[73] Assignee: Slurry Liquidator Corp., Mancos, Colo.

[21] Appl. No.: 794,484

[22] Filed: Feb. 4, 1997

[51] Int. Cl.⁶ .................................................. A61L 9/00
[52] U.S. Cl. ........................... 422/5; 422/5; 422/123; 422/306
[58] Field of Search ............................. 422/5, 305, 306, 422/123

[56] References Cited

U.S. PATENT DOCUMENTS

| | | | |
|---|---|---|---|
| 3,720,290 | 3/1973 | Lansky et al. | 184/6.26 |
| 5,308,589 | 5/1994 | Yung | 422/169 |
| 5,417,920 | 5/1995 | Yung | 422/5 |

Primary Examiner—Robert J. Warden
Assistant Examiner—Fariborz Moazzam
Attorney, Agent, or Firm—John B. Phillips; John R. Ley

[57] ABSTRACT

A method and apparatus for deodorizing the pungent airflow exhausted by a vacuum pump system while evacuating foul smelling liquids or liquid-solid mixtures from a holding tank such as a septic tank or a grease trap. A manifold is connected to the vacuum pump to receive the airflow exhausted by the vacuum pump. At least one nozzle is attached to the manifold so that a distal end of the nozzle extends into the airflow passing through the manifold. A reservoir supplies a concentrated liquid deodorizer to the nozzle during operation of the vacuum pump. The liquid deodorizer is dispersed by the distal end of the nozzle and mixes with the airflow within the manifold to deodorize the airflow before the airflow is exhausted to the ambient atmosphere. The distal end of the nozzle which extends into the airflow is tapered to substantially atomize the liquid deodorizer and enhance the mixture of the liquid deodorizer with the airflow. The deodorizing method and apparatus may be installed on any existing vacuum pump system.

16 Claims, 2 Drawing Sheets

VACUUM PUMP DEODORIZING APPARATUS AND METHOD

FIELD OF THE INVENTION

This invention relates generally to a new and improved method and apparatus for deodorizing the exhaust airflow from vacuum pump systems used, for example, to evacuate pungent liquids or liquid-solid mixtures from holding tanks, pits, reservoirs and the like.

BACKGROUND OF THE INVENTION

Vacuum pump systems are frequently used to empty caustic liquids and liquid-solid mixtures from holding tanks and to transport those substances for disposal. Vacuum pump systems utilize a vacuum pump which is typically attached to a vacuum tank by a first hose. The vacuum pump is used to continuously evacuate air from the vacuum tank. A second hose, attached to a valve of the vacuum tank, is inserted into the holding tank, pit or the like and the vacuum created in the vacuum tank transfers the substances from the holding tank to the vacuum tank. As the liquid fills the vacuum tank, fumes within the vacuum tank, together with air and fumes from the holding tank, are continuously evacuated from the vacuum tank through the first hose and are ultimately expelled to the atmosphere after passing through the vacuum pump and an exhaust port or muffler of the vacuum pump. While the vacuum pump system typically includes one or more filters to remove dirt and debris from the air before it can enter the vacuum pump, such filters are not effective for removing odors from the air.

Thus, during operation of the vacuum pump, any noxious odors contained within the holding tank or released from the substances pumped into the vacuum tank are exhausted into the atmosphere surrounding the vacuum pump system. The odors carried by the substances pumped into the vacuum tank are frequently pungent and often permeate the ambient atmosphere. These odors may be extremely unpleasant and could potentially be unhealthy. For example, when large truck-mounted vacuum pump systems are used to empty residential septic tanks, the residents may be exposed to concentrated sewage odors. Additionally, when smaller, more portable vacuum pump systems are used within a residence or business, such as to clean a grease trap within a restaurant's kitchen, the exhaust from the vacuum pump may contaminate the restaurant's atmosphere with the unpalatable smell from the grease trap.

While deodorizing sprays and room fresheners may be used to help combat the offending odors when a portable vacuum pump system is used indoors, such deodorizing sprays are not capable of overcoming the odors of the airflow being exhausted from the vacuum pump. Of course, such room deodorizers can not be used effectively outdoors with larger vacuum pump systems.

It is with respect to these and other background considerations, limitations and problems, that the technique of the present invention has evolved.

SUMMARY OF THE INVENTION

One of the significant aspects of the present invention pertains to an apparatus for deodorizing the airflow exhausted by a vacuum pump system which is used to remove pungent smelling substances from a holding tank. The apparatus of the present invention utilizes a manifold connected in the air flow path of a vacuum pump. The manifold is positioned so that the vacuum pump airflow must pass through the manifold before being exhausted to the atmosphere. One or more nozzles are attached to the manifold so that a distal end of each nozzle extends into airflow which passes through the interior of the manifold. A reservoir contains a supply of concentrated liquid deodorizer and a pump or gravity is used to deliver a steady supply of the liquid deodorizer to each nozzle during operation of the vacuum pump. The liquid deodorizer flows from the distal ends of each nozzle and thoroughly disburses within the airflow passing through the manifold to deodorize the airflow before the airflow is exhausted.

Another significant aspect of the present invention relates to the tapering of the distal end of each nozzle which extends within the airflow in the manifold to enhance the dispersal of the liquid deodorizer in the airflow. Each nozzle tip is preferably tapered so that the liquid deodorizer exits the nozzle from an opening which faces downstream within the manifold relative to the direction of the airflow. The tapered nozzle tip operates to substantially atomize the liquid deodorizer as it enters the airflow and thus enhances mixture of the deodorizer with the airflow.

A further significant aspect of the present invention pertains to a vacuum pump system deodorizing apparatus which may be installed on any existing vacuum pump system. Manifolds of varying size and orientation may be placed in the airflow path, preferably between the vacuum pump and the muffler of the vacuum pump system, and one or more deodorizer nozzles may be utilized depending on the size of the vacuum pump and the manifold.

Another significant aspect of the present invention relates to a method of adding a deodorizing apparatus to an existing vacuum pump system by connecting the manifold in the vacuum pump exhaust airflow path, preferably between the vacuum pump and the muffler; connecting the deodorizer reservoir to one or more deodorizer nozzles; and orienting the nozzles within the manifold for mixture of the liquid deodorizer with the airflow during operation of the vacuum pump.

A more complete appreciation of the present invention and its scope may be obtained from the accompanying drawings, which are briefly summarized below, from the following detailed descriptions of presently preferred embodiments of the invention, and from the appended claims.

DETAILED DESCRIPTION OF THE DRAWING

DETAILED DESCRIPTION OF THE PREFERRED EMBODIMENT

The present invention may be applied to a variety of vacuum pump systems used to evacuate liquids or liquid-solid mixtures from holding tanks, reservoirs, pits and the like. While these vacuum pump systems may range in size, depending on the size and location of the holding tank to be emptied, the present invention is shown attached to a relatively large, trailer-mounted vacuum pump system 20 such as would typically be used to clean out a residential septic tank (not shown). The present invention may also be truck-mounted or skid-mounted, and smaller versions may be attached to hand manipulated dolly such as those which are moved into restaurants to evacuate grease pits, for example.

Figure 1:
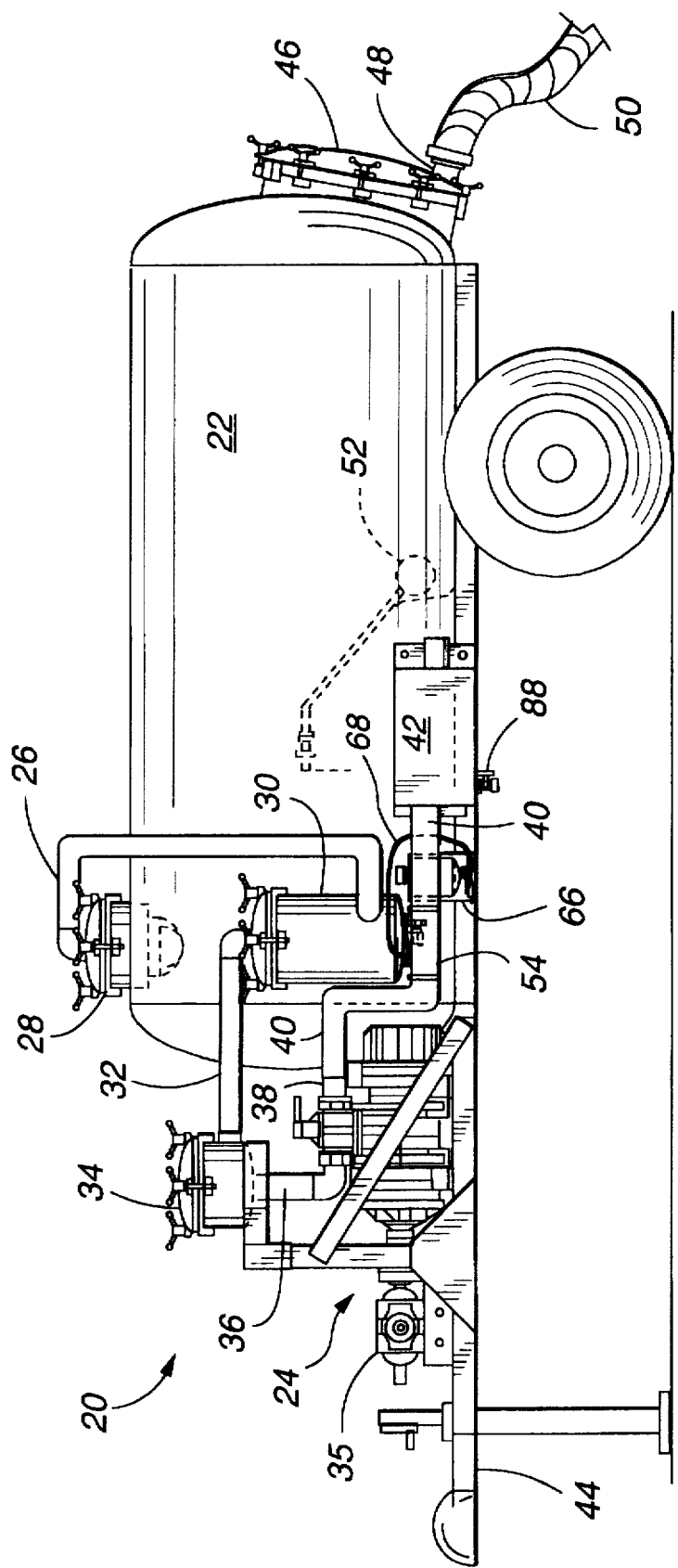
FIG. 1 is a side elevation view of a trailer-mounted vacuum pump system which includes a vacuum tank, vacuum pump which expels evacuated air from the vacuum tank, a muffler and a deodorizer apparatus of the present invention.

The vacuum pump system 20 shown in FIG. 1 includes a vacuum tank 22 and a vacuum pump 24. A first air hose 26 connects a primary shut-off 28 on top of the tank 22 to a secondary shut-off 30 positioned to the side of the tank 22. A second air hose 32 connects the secondary shut-off 30 to a filter 34, while a third air hose 36 connects the filter 34 to the vacuum pump 24. Power for operating the vacuum pump is applied from a motor (not shown) which drives the vacuum pump through a power input delivery unit 35. Operation of the vacuum pump 24 tends to draw air through the air hoses 26, 32 and 36 from the vacuum tank 22 to create at least a partial vacuum in the tank 22.

As the vacuum pump 24 evacuates air from the tank 22, the airflow from the tank 22 enters the vacuum pump 24 from the air hose 36 and is ultimately expelled through an exhaust port 38 of the pump 24. An exhaust hose 40 typically connects the exhaust port 38 to a muffler 42, as shown in FIG. 1. Thus, air which is evacuated from the vacuum tank 22 is ultimately expelled to the atmosphere after passing through the vacuum pump 24 and the muffler 42.

The vacuum tank 22, vacuum pump 24 and the muffler 42 are all preferably mounted on a trailer 44, as shown in FIG. 1. The trailer 44 may be positioned adjacent a holding tank, such as a septic tank (not shown), which is to be emptied. A manway 46 on the rear of the vacuum tank 22 includes a valve 48 which provides access to the bottom of the tank 22. A vacuum hose 50 is attached at one end to the valve 48 so that its free end may be inserted into the holding tank (e.g., the septic tank, not shown).

Once the vacuum hose 50 is properly positioned in the liquid or liquid-solid substance within the holding tank (not shown), the vacuum pump 24 is activated to evacuate the air from the vacuum tank 22 as well as the air contained within the vacuum hose 50. As the air pressure within the tank 22 drops, the substance within the holding tank (not shown) begins to migrate through the vacuum hose 50 and the valve 48 and into the bottom of the tank 22. As the substance fills the tank 22, a level indicator such as the float 52 (shown in phantom in FIG. 1) operates in a conventional manner to measure the level of the substance within the tank.

During the evacuation process, odors emanating from the substance contained in the holding tank will tend to be evacuated from the tank 22 along with the air flowing to the vacuum pump 24. Although the filter 34 helps to prevent dirt or debris from being sucked through the hoses 26 and 36 and into the vacuum pump 24, the filter 34 can not filter out noxious odors from the airflow. Rather, such odors would typically be expelled along with the airflow from the muffler 42.

Figure 2:
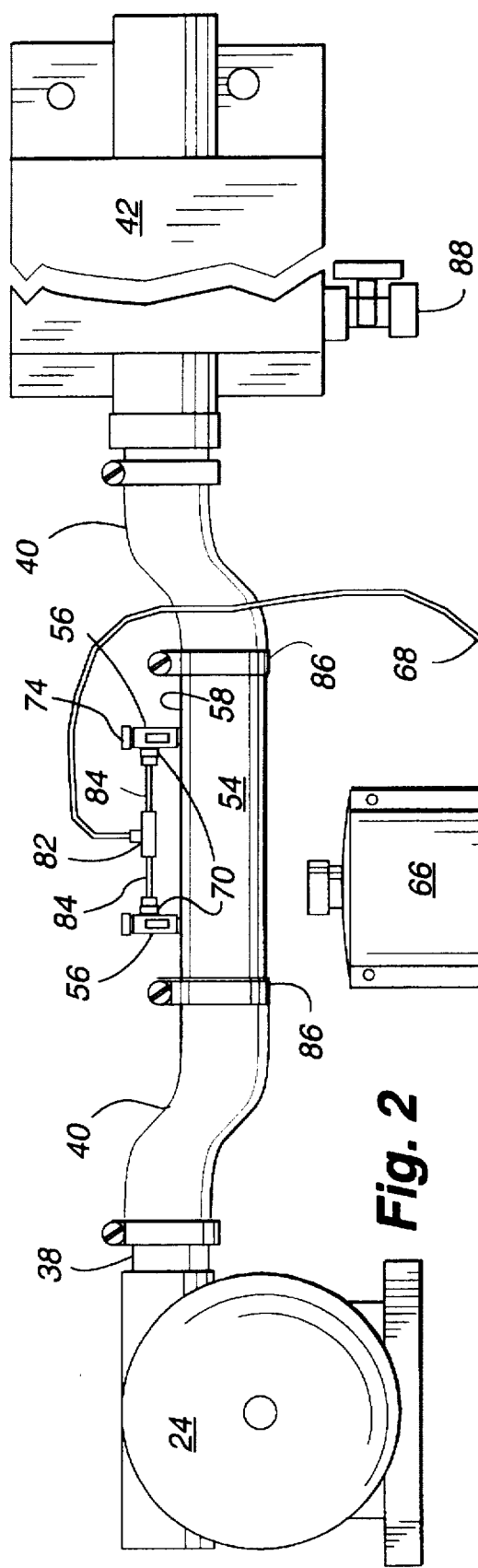
FIG. 2 is an enlarged side elevation view of a deodorizer reservoir and deodorizer manifold of the deodorizer apparatus of the present invention, shown in its preferred position between the vacuum pump and the muffler of the vacuum pump system illustrated in FIG. 1.

As shown in FIG. 2, the preferred embodiment of the present invention includes a manifold 54 positioned along the exhaust hose 40 between the exhaust port 38 of the vacuum pump 24 and the muffler 42. The manifold 54 is preferably formed from a metal cylinder similar to conventional air ducts. The length and diameter dimensions of the manifold 54 accommodate fitting the manifold 54 between the vacuum pump exhaust port 38 and the muffler 42 according to the size and capacity of the vacuum pump system. The typical size of the manifold on the majority of larger vacuum pump system would be approximately 12 inches long and approximately 2–3 inches in diameter. Of course, the size of the manifold 54 may be scaled either up or down depending on the size of the vacuum pump system.

Figure 3:
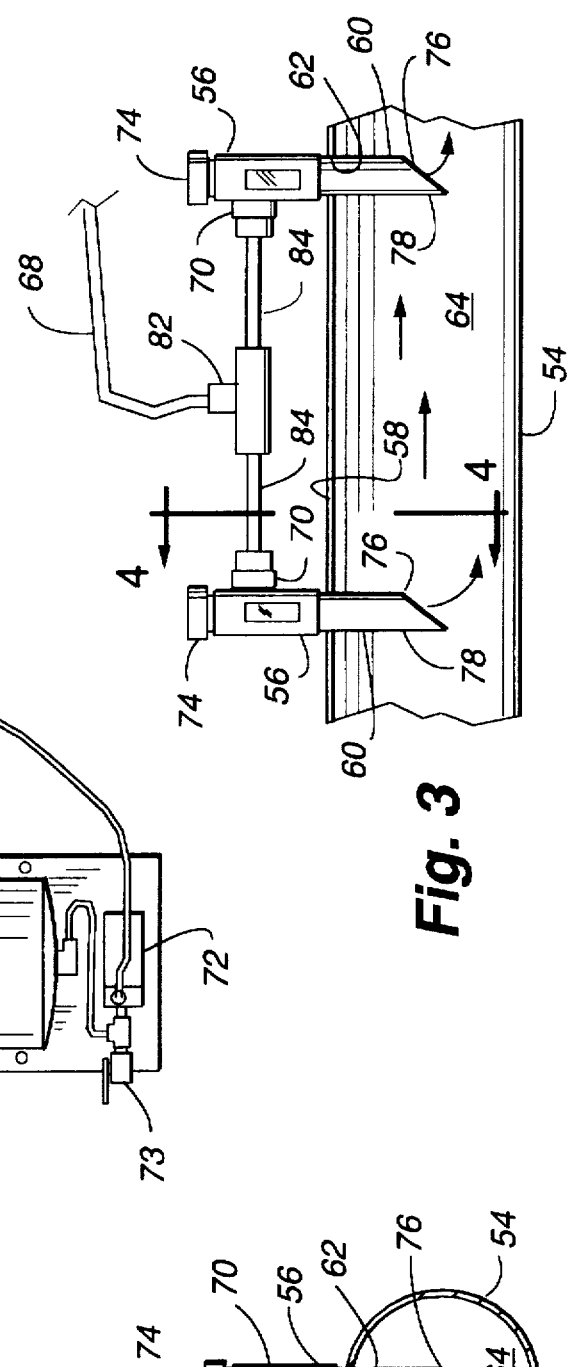
FIG. 3 is an enlarged section view taken axially through the deodorizer manifold shown in FIG. 2.
Figure 4:
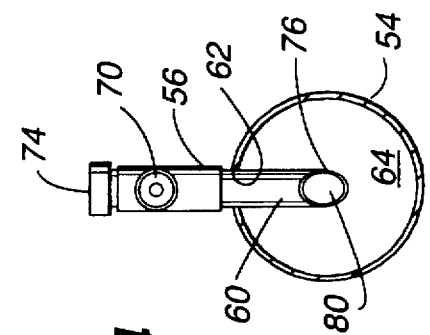
FIG. 4 is a cross-section view taken substantially in the plane of line 4—4 of FIG. 3.

At least one deodorizer nozzle 56 (FIGS. 2–4) is attached to a top or exterior surface 58 of the manifold 54. A distal end 60 of the nozzle 56 fits through an opening 62 formed in the top surface 58 of the manifold 54 and extends into an open interior section 64 of the manifold 54, as shown in FIGS. 3 and 4. The nozzle 56 is held permanently in place such as by welding it to the manifold 54, for example.

A deodorizer reservoir 66 (FIGS. 1 and 2) contains a supply of a concentrated liquid deodorizer to be delivered to the deodorizer nozzle 56. A deodorizer hose 68 connects the reservoir 66 to an inlet 70 of the nozzle 56 to supply the liquid deodorizer to the nozzle. While the deodorizer reservoir 66 may be positioned above the nozzle 56 to allow the liquid deodorizer to drain by gravity to the nozzle 56, the preferred embodiment of the present invention includes a separate injector pump 72 attached to the reservoir 66. The injector pump 72 operates to pump a steady supply of the liquid deodorizer to the inlet 70 of the nozzle 56, regardless of the relative positions of the nozzle 56 and the reservoir 66 (i.e., the reservoir 66 may be placed at or below the level of the nozzle 56). A drain valve 73 (FIG. 2) at the bottom of the reservoir 66 is available to drain unused deodorizer liquid from the reservoir 66.

The liquid deodorizer supplied to the inlet 70 of the deodorizer nozzle 56 from the reservoir 66 flows through the nozzle 56 to its distal end 60 and into the open interior 64 of the manifold 54 as shown in FIGS. 3 and 4. However, the deodorizer nozzle 56 includes a conventional flow restriction valve 74 to meter the flow of the liquid deodorizer received from the reservoir 66. An external adjustment knob of the valve 74 may be turned to alternately open and close the flow restriction valve within the nozzle 56 and thereby control the rate at which the liquid deodorizer enters the nozzle 56. As explained in greater detail below, a predetermined rate of delivery of the liquid deodorizer into the open interior 64 of the manifold 54 is selected to enhance the mixture of the liquid deodorizer with the airflow passing through the manifold 54 and thereby achieve an optimum deodorizing effect.

Once the manifold 54 is connected into the exhaust hose 40, as shown in FIG. 2, the injector pump 72 may be activated at any time during the operation of the vacuum pump 24 to deliver the liquid deodorizer from the nozzle 56 into the airflow which is exhausted from the muffler 42. The dispersal of the liquid deodorizer into the airflow passing through the manifold 54 tends to reduce or mask the natural odor generated by the substance which is being evacuated from the holding tank (not shown).

The performance of the deodorizing apparatus is enhanced when the liquid deodorizer is thoroughly mixed with the airflow within the manifold 54. Thus, the distal end 60 of the deodorizer nozzle 56 preferably includes a tapered tip 76 at its free end, as shown in FIGS. 3 and 4. The tapered tip 76 tapers from its full diameter to a narrow end as the tip 76 extends into the open interior 64 of the manifold 54. Additionally, the narrow end of the tapered tip 76 is preferably positioned along an upstream side 78 of the distal end 60 of the nozzle 56 to form an opening 80 (FIG. 4) which faces downstream within the open interior 64 of the manifold 54.

Positioning the tapered tip 76 in such a manner, with the opening 80 facing in the downstream direction, tends to disperse the liquid deodorizer in an atomized mist into the airflow within the manifold 54. In effect, the upstream side of the tapered tip blocks the airflow through the manifold and thus acts to form a pocket of low pressure immediately downstream of the narrow end of the tapered tip and substantially at the point where the liquid deodorizer emerges from the opening 80. The differential in air pressure between the main airflow within the open interior 64 of the manifold 54 and the opening 80 from which the liquid deodorizer emerges tends to atomize the liquid deodorizer into a fine mist and further enhances the mixture of the deodorizer mist with the airflow. Of course, alternative atomizing or mist creating means may be used. For example, rather than tapering the distal end 60 of the nozzle 56, a non-tapered distal end may be bent in the downstream direction. As a further alternative, a high pressure spray may be employed within the manifold 54. Thus, while the preferred embodiment uses the tapered tip 76 shown in FIGS. 3 and 4, the broader aspects of the present invention encompasses any nozzle or spray which facilitates atomizing and thoroughly mixing the liquid deodorizer with the airflow through the manifold 54.

The flow rate of the liquid deodorizer through the nozzle 56 is preferably adjusted so that a continuous flow of liquid deodorizer is substantially atomized and thus thoroughly mixed with the airflow prior to being exhausted to the atmosphere by the muffler 42. Furthermore, the amount of liquid deodorizer delivered may be adjusted according to the pungency of the odor, to avoid using more deodorizer than is required. Once the nozzle 56 is properly adjusted, the substantial atomization of the liquid deodorizer within the manifold 54 helps to ensure a consistent level of performance by thoroughly mixing the liquid deodorizer with the airflow to reduce or mask the otherwise pungent odors which are naturally exhausted with the airflow from the muffler 42.

In the case of relatively large vacuum pump systems, such as the trailer-mounted system 20 shown in FIGS. 1–4, a single deodorizer nozzle 56 may be insufficient to provide an adequate level of deodorization of the relatively large volume of air exhausted. In such circumstance, two or more separate nozzles 56 may be positioned along the length of the manifold 54, as shown in FIGS. 2 and 3.

A union tee 82 (or other distribution means) is used to fluidly connect the two (or multiple) nozzles 56, as shown in FIG. 3, by connecting a first tube 84 between one of the nozzle inlets 70 and one arm of the union tee 82 and a second tube 84 between the other nozzle inlet 70 and a second arm of the union tee 82. The deodorizer hose 68 from the reservoir 66 then attaches to a third arm of the union tee 82 to provide a steady supply of liquid deodorizer to both nozzles 56. Of course, additional nozzles could be added to the manifold 54 in a similar fashion.

The manifold 54 is preferably placed at a lower position than the level of the vacuum pump exhaust port 38 to help prevent a back flow of the liquid deodorizer into the vacuum pump. However, subject to this limitation, the manifold 54 may be positioned as required to fit between the vacuum pump 24 and the muffler 42. For example, the manifold 54 could be positioned vertically so that the airflow through the open interior 64 of the manifold travels vertically downward toward the muffler 42. The nozzle or nozzles 56 would then be inserted horizontally through the exterior surface of the manifold 54 so that the opening 80 at the tapered tip 76 of each nozzle faces vertically downward (i.e., downstream) to achieve the above-described beneficial mixing with the airflow due to the substantial atomization of the liquid deodorizer.

The deodorizing apparatus described above may be beneficially used with any vacuum pump system where noxious odors may be expelled during the evacuation of a liquid or a liquid-solid mixture. The manifold 54 may be sized and positioned as required to fit any vacuum pump system. Additionally, one or more nozzles 56 may be utilized to provide an optimal level of deodorization, depending on the size of the manifold and the level of the noxious odors produced by the liquid or the liquid-solid substance to be evacuated.

Furthermore, the manifold 54, the reservoir 66, injector pump 72, and one or more nozzles 56 may be sold together, as a deodorizer kit, along with the necessary connectors such as the hoses 68 and 84, the union tee 82 and hose clamps 86 for attaching the manifold 54 to the exhaust line 40. Such a deodorizer kit would be available in different sizes and configurations to allow the deodorizer apparatus to be retrofitted on to any existing vacuum pump system.

The present invention also encompasses a method of deodorizing the airflow exhausted by a vacuum pump system by installing the manifold 54, nozzles 56, reservoir 66 and their associated elements on an existing vacuum pump system and operating those components with the vacuum pump system in the manner described. The method includes connecting the manifold 54 between the exhaust port 38 of the vacuum pump 24 and the muffler 42 by severing the exhaust hose 40 and inserting the manifold 54 between the severed ends of the exhaust hose 40. Conventional hose clamps 86 (FIG. 2) are used to attach the ends of the manifold 54 to the severed ends of the exhaust hose 40. If necessary, a length of the exhaust hose equal to the length of the manifold 54 may be removed to provide sufficient space for the insertion of the manifold 54.

Next, the distal ends 60 of one or more nozzles 56 are inserted through an exterior surface of the manifold 54 so that the opening 80 formed by the tapered tip 76 of each nozzle faces downstream within the open interior 64 of the manifold 54. Alternatively, the nozzles 56 may be preattached to the manifold 54 so that the manifold need only be properly oriented (with the openings 80 facing downstream in the direction of the muffler 62) prior to inserting the manifold between the ends of the exhaust hose 40. The inlets 70 of each of the nozzles 56 are then connected to the deodorizer reservoir 66 and, if necessary, an injector pump 72 is connected between the reservoir 66 and the nozzles 56 to ensure a steady flow of liquid deodorizer to the nozzles. The nozzles are then adjusted to allow the liquid deodorizer to flow to the openings 80 within the open interior 64 of the manifold 54 at a predetermined rate during operation of the vacuum pump 24 to thoroughly mix the liquid deodorizer with the airflow before the airflow is exhausted from the muffler.

Additionally, the muffler 42 will typically be an oil catch muffler. After operation of the vacuum pump system (i.e., when the holding tank has been emptied), a valve 88 at the bottom of the oil catch muffler 42 may be opened to drain any excess liquid deodorizer or other liquid that may have collected within the muffler 42. A portion of the atomized liquid deodorizer may have condensed out of the airflow into the muffler 42 during operation of the vacuum pump 24 prior to being exhausted from the muffler 42.

Thus, the method of the present invention allows for the above-described deodorizing apparatus to be installed on any existing vacuum pump system, regardless of its size or orientation. Such a method will provide a great benefit to those who operate vacuum pump systems for the removal of pungent liquids or liquid-solid mixtures, as well as to those who live or work in the immediate area and who would otherwise be offended by the odor created during the removal process.

A presently preferred embodiment of the present invention has been described above with a degree of specificity. It should be understood, however, that this degree of specificity is directed toward the preferred embodiment. The invention itself is defined by the scope of the appended claims.

The invention claimed is:

1. A method of modifying a mobile vacuum pump system to deodorize pungent odors exhausted by the vacuum pump system, said mobile vacuum pump system including a vacuum hose having a first end for insertion into a holding tank containing a pungent material, a vacuum tank connected to an opposite end of the vacuum hose for receiving the pungent material evacuated from the holding tank, a vacuum pump for evacuating air from the vacuum tank and the vacuum hose to draw the pungent material from the holding tank into the vacuum tank through the vacuum hose, a muffler for exhausting the air evacuated from the vacuum tank and the vacuum hose, and an exhaust hose fluidly connecting the vacuum pump to the muffler, said vacuum pump creating an airflow through the vacuum hose, the vacuum tank, the vacuum pump, the exhaust hose and the muffler, said method comprising the steps of:

severing the exhaust hose at a point between the vacuum pump and the muffler to create opposing severed ends of the exhaust hose;

attaching a manifold between the opposing severed ends of the exhaust hose to receive the airflow exhausted by the vacuum pump, said manifold having an open interior through which the airflow flows to the muffler;

inserting a distal end of a nozzle through an opening formed in an exterior surface of the manifold;

extending the distal end of the nozzle into the open interior of the manifold and orienting an opening in the distal end of the nozzle to face downstream in relation to the airflow through the manifold;

fixedly attaching the nozzle to the manifold to maintain the position of the distal end of the nozzle within the open interior of the manifold;

connecting a deodorizer reservoir to an inlet at a proximal end of the nozzle to deliver liquid deodorizer to the nozzle;

adjusting the inlet to deliver a predetermined flow of the liquid deodorizer to the distal end of the nozzle; and creating a substantially atomized spray of the liquid deodorizer by emitting the liquid deodorizer from the downstream-facing nozzle opening as the airflow passes the distal end of the nozzle, said atomized spray dispersing within the airflow proceeding through the open interior of the manifold.

2. A method as defined in claim 1, further comprising the step of:

mounting the mobile vacuum pump system on a truck.

3. A method as defined in claim 1, further comprising the step of:

cutting the distal end of the nozzle at an angle to form the opening facing downstream in relation to the airflow through the manifold.

4. A method as defined in claim 1, further comprising the step of:

positioning the reservoir above the manifold to allow the liquid deodorizer to gravity drain from the reservoir to the nozzle inlet.

5. A method as defined in claim 1, further comprising the step of:

pumping the liquid deodorizer from the reservoir to the nozzle inlet.

6. A method as defined in claim 1, further comprising the steps of:

inserting a distal end of a second nozzle through a second opening formed in the exterior surface of the manifold;

extending the distal end of the second nozzle into the open interior of the manifold and orienting an opening in the distal end of the second nozzle to face downstream in relation to the airflow through the manifold;

fixedly attaching the second nozzle to the manifold to maintain the position of the distal end of the second nozzle within the open interior of the manifold;

connecting the deodorizer reservoir to an inlet at a proximal end of the second nozzle to deliver liquid deodorizer to the second nozzle;

adjusting the inlet to deliver a predetermined flow of the liquid deodorizer to the distal end of the second nozzle; and creating a substantially atomized spray of the liquid deodorizer by emitting the liquid deodorizer from the downstream-facing opening in the second nozzle as the airflow passes the distal end of the second nozzle, said substantially atomized spray dispersing within the airflow proceeding through the open interior of the manifold.

7. A method as defined in claim 1, further comprising the step of:

draining liquid deodorizer which condenses out of the airflow and collects in the muffler prior to being exhausted with the airflow from the muffler.

8. An improved mobile vacuum pump system for removing pungent material from a holding tank, said mobile vacuum pump system including a vacuum hose having a first end for insertion into the holding tank containing the pungent material, a vacuum tank connected to an opposite end of the vacuum hose for receiving the pungent material evacuated from the holding tank, a vacuum pump for evacuating air from the vacuum tank and the vacuum hose to draw the pungent material from the holding tank into the vacuum tank through the vacuum hose, a muffler for exhausting the air evacuated from the vacuum tank and the vacuum hose, and an exhaust hose fluidly connecting the vacuum pump to the muffler, said vacuum pump creating an airflow through the vacuum hose, the vacuum tank, the vacuum pump, the exhaust hose and the muffler, wherein the improvement comprises:

a manifold connected to the exhaust hose at a position between the vacuum pump and the muffler to receive the airflow exhausted by the vacuum pump, said manifold having an open interior through which the airflow flows to the muffler;

a nozzle fixedly attached to the manifold, said nozzle including a distal end extending through an opening formed in an exterior surface of the manifold, said distal end of the nozzle extending into the open interior of the manifold, and said distal end having an opening which is oriented in a downstream direction in relation to the airflow through the manifold;

a deodorizer reservoir in fluid communication with a proximal end of the nozzle to deliver liquid deodorizer to the nozzle; and a variable inlet at the proximal end of the nozzle to deliver a predetermined flow of the liquid deodorizer to the distal end of the nozzle, said distal end creating a substantially atomized spray of the liquid deodorizer and disperse the substantially atomized spray into the airflow proceeding through the open interior of the manifold as the airflow passes the downstream-facing nozzle opening.

9. An improved mobile vacuum pump system as defined in claim 8, wherein:

the vacuum tank, the vacuum pump, the manifold, the nozzle, the reservoir and the muffler are mounted on a truck.

10. An improved mobile vacuum pump system as defined in claim 8, wherein:

the distal end of the nozzle is cut at an angle to form the opening oriented in the downstream direction in relation to the airflow through the manifold.

11. An improved mobile vacuum pump system as defined in claim 8, wherein:

the reservoir is positioned above the manifold to provide gravity drainage of the liquid deodorizer from the reservoir to the nozzle inlet.

12. An improved mobile vacuum pump system as defined in claim 8, wherein the improvement further comprises:

a pump to pump the liquid deodorizer from the reservoir to the nozzle inlet.

13. An improved mobile vacuum pump system as defined in claim 8, wherein:

the muffler is an oil catch muffler for collecting liquid deodorizer which condenses out of the airflow prior to being exhausted with the airflow from the muffler, said oil catch muffler including a drain for draining the collected liquid deodorizer.

14. An improved mobile vacuum pump system as defined in claim 8, wherein:

the manifold extends in a substantially horizontal direction between the vacuum pump and the muffler;

the distal end of the nozzle extends substantially vertically into the open interior of the manifold from a top exterior surface of the manifold; and the top surface of the manifold is positioned lower than the vacuum pump to prevent liquid deodorizer from flowing back into the vacuum pump.

15. An improved mobile vacuum pump system as defined in claim 8, wherein the improvement further comprises:

a second nozzle fixedly attached to the manifold, said second nozzle including a distal end extending through a second opening formed in an exterior surface of the manifold, said distal end of the second nozzle extending into the open interior of the manifold, and said distal end having an opening which is oriented in a downstream direction in relation to the airflow through the manifold;

a variable inlet at the proximal end of the second nozzle, said variable inlet connected to the reservoir to deliver a predetermined flow of the liquid deodorizer to the distal end of the second nozzle, said distal end creating a substantially atomized spray of the liquid deodorizer and disperse the substantially atomized spray into the airflow proceeding through the open interior of the manifold as the airflow passes the downstream-facing opening of the second nozzle.

16. An improved mobile vacuum pump system as defined in claim 15, wherein:

the manifold extends in a substantially horizontal direction between the vacuum pump and the muffler;

the distal ends of the first aforesaid nozzle and the second nozzle extend substantially vertically into the open interior of the manifold from a top exterior surface of the manifold; and the top surface of the manifold is positioned lower than the vacuum pump to prevent liquid deodorizer from flowing back into the vacuum pump.

* * * * *